United States Patent
Miller et al.

(10) Patent No.: US 6,479,298 B1
(45) Date of Patent: Nov. 12, 2002

(54) DEVICE AND METHOD FOR SEPARATING COMPONENTS OF A FLUID SAMPLE

(75) Inventors: Henry F. Miller, Clifton, NJ (US); Fu-Chung Lin, Wayne, NJ (US); Robert J. Losada, Astoria, NY (US); Jeffrey P. Radziunas, Wallingford, CT (US); Jeffrey Karg, Hopkinton, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/454,988

(22) Filed: Dec. 3, 1999

Related U.S. Application Data

(60) Provisional application No. 60/110,934, filed on Dec. 5, 1998, and provisional application No. 60/110,928, filed on Dec. 5, 1998.

(51) Int. Cl.$^7$ .................................................. G01N 1/18
(52) U.S. Cl. ...................... 436/177; 436/174; 422/101; 210/121; 210/122
(58) Field of Search .................. 436/177, 174; 210/740, 781, 782, 121, 122, 123, 242.1, 329, 513; 422/101

(56) References Cited

U.S. PATENT DOCUMENTS

| | | | | |
|---|---|---|---|---|
| 3,882,021 A | * | 5/1975 | Ayres | 210/136 |
| 3,887,464 A | * | 6/1975 | Ayres | 210/117 |
| 3,887,466 A | * | 6/1975 | Ayres | 210/131 |
| 3,890,237 A | * | 6/1975 | Welch | 210/516 |
| 3,891,553 A | * | 6/1975 | Ayres | 210/136 |
| 3,894,950 A | | 7/1975 | Ayres et al. | |
| 3,897,343 A | * | 7/1975 | Ayres | 210/516 |
| 3,909,419 A | | 9/1975 | Ayres | |
| 3,957,654 A | * | 5/1976 | Ayres | 210/516 |
| 4,152,270 A | | 5/1979 | Cornell | |
| 4,294,707 A | * | 10/1981 | Ikeda et al. | 210/782 |
| 4,315,892 A | * | 2/1982 | Stone et al. | 422/101 |
| 4,417,981 A | | 11/1983 | Nugent | |
| 4,853,137 A | | 8/1989 | Ersson | |
| 5,271,852 A | * | 12/1993 | Luoma et al. | 210/789 |
| 5,455,009 A | | 10/1995 | Vogler et al. | |
| 6,063,297 A | | 5/2000 | Antanavich et al. | |

* cited by examiner

*Primary Examiner*—Jill Warden
*Assistant Examiner*—Yelena Gakh
(74) *Attorney, Agent, or Firm*—Nanette S. Thomas

(57) ABSTRACT

A device and method for separating heavier and lighter fractions of a fluid sample. The device includes a plurality of constituents comprising a container and a composite element in the container. The composite element is a separator comprising at least two components and more particularly, a bellows with a seal body, a low-density float and a high-density ballast. A fluid sample is delivered to the container and the device is subjected to centrifugation whereby the centrifugal load causes the seal body of the separator to deform so that the separator migrates through the fluid sample and then stabilizes between the heavier and lighter fractions of the fluid sample. The seal body of the separator will resiliently return to its initial configuration upon termination of the centrifugal load such that the seal body sealingly engages the container and the composite element separates the heavier and lighter fractions of the fluid sample.

17 Claims, 13 Drawing Sheets

DEVICE AND METHOD FOR SEPARATING COMPONENTS OF A FLUID SAMPLE

This application claims benefit of provisional applications Nos. 60/110934, filed Dec. 5, 1998, and 60/110928, filed Dec. 5, 1998.

BACKGROUND OF THE INVENTION

1. Field of the Invention

This invention relates to a device and method for separating heavier and lighter fractions of a fluid sample. More particularly, this invention relates to a device and method for collecting and transporting fluid samples whereby the device and fluid sample are subjected to centrifugation in order to cause separation of the heavier fraction from the lighter fraction of the fluid sample.

2. Description of Related Art

Diagnostic tests may require separation of a patient's whole blood sample into components, such as serum or plasma, the lighter phase component, and red blood cells, the heavier phase component. Samples of whole blood are typically collected by venipuncture through a cannula or needle attached to a syringe or an evacuated collection tube. Separation of the blood into serum or plasma and red blood cells is then accomplished by rotation of the syringe or tube in a centrifuge. Such arrangements use a barrier for moving into an area adjacent the two phases of the sample being separated to maintain the components separated for subsequent examination of the individual components.

A variety of devices have been used in collection devices to divide the area between the heavier and lighter phases of a fluid sample.

The most widely used device includes thixotropic gel materials such as polyester gels in a tube. The present polyester gel serum separation tubes require special manufacturing equipment to prepare the gel and to fill the tubes. Moreover, the shelf-life of the product is limited in that overtime globules may be released from the gel mass. These globules have a specific gravity that is less than the separated serum and may float in the serum and may clog the measuring instruments, such as the instrument probes used during the clinical examination of the sample collected in the tube. Such clogging can lead to considerable downtime for the instrument to remove the clog.

No commercially available gel is completely chemically inert to all analytes. If certain drugs are present in the blood sample when it is taken, there can be an adverse chemical reaction with the gel interface.

Therefore, a need exists for a separator device that (i) is easily used to separate a blood sample; (ii) is independent of temperature during storage and shipping; (iii) is stable to radiation sterilization; (iv) employs the benefits of a thixotropic gel barrier yet avoids the many disadvantages of placing a gel in contact with the separated blood components; (v) minimizes cross contamination of the heavier and lighter phases of the sample during centrifugation; (vi) minimizes adhesion of the lower and higher density materials against the separator device; (vii) is able to move into position to form a barrier in less time than conventional methods and devices; (viii) is able to provide a clearer specimen with less cell contamination than conventional methods and devices; and (ix) can be used with standard sampling equipment.

SUMMARY OF THE INVENTION

The present invention is a method and assembly for separating a fluid sample into a higher specific gravity phase and a lower specific gravity phase. Desirably, the assembly of the present invention comprises a plurality of constituents. Preferably, the assembly comprises a container and a composite element.

Most preferably, the container is a tube and the composite element is a separator arranged to move in the tube under the action of centrifugal force in order to separate the portions of a fluid sample.

Most preferably, the tube comprises an open end, a closed end and a sidewall extending between the open end and closed end. The sidewall comprises an outer surface and an inner surface. The tube further comprises a closure disposed to fit in the open end of the tube with a resealable septum. Alternatively, both ends of the tube may be open, and both ends of the tube may be sealed by elastomeric closures. At least one of the closures of the tube may include a resealable septum.

Preferably, the separator element is releaseably positioned at the open end of the tube with the closure. Alternatively, the separator element may also be releasably positioned at the closed end of the tube.

Preferably, the closure may further include a bottom recess that extends into the tube having a plurality of inwardly extending circumferentially spaced flexible walls or a flexible full ring for holding the separator.

Preferably, the separator element comprises an overall specific gravity at a target specific gravity of $\sigma_t$. The target specific gravity is that required to separate a fluid sample into at least two phases.

Preferably, the separator comprises at least two or more regions of differing specific gravities. Preferably, at least one of the regions is higher than the target specific gravity and at least one of the regions is lower than the target specific gravity.

Preferably, the separator element comprises a toroid or a bellows, a foam or a float and a sinker or a ballast. The bellows comprises opposed first and second ends and a seal body extending between the ends. The outer diameter of the seal body is larger than the inner diameter of the tube for sealing engagement. Most preferably, the seal body has elastic properties.

Most preferably the float is securely mounted to the first end of the bellows and the ballast is securely mounted to the second end of the bellows.

Alternatively, the bellows comprises a first end that is a resealable septum and an open second end.

Preferably, the separator may be initially located at any position within the tube. Most preferably, the separator is held in position at the top of the tube by an interference fit between the seal body and the tube inner diameter.

Preferably, the separator has central passageway that extends from the first end through the seal body and to the second end of the bellows.

Preferably, the bellows has a specific gravity of about 0.8 to about 1.2. Most preferably, the bellows is made from an elastomer which has a 50% tensile modulus (YOUNGS) from about 100 psi to about 500 psi.

Desirably, the seal body may be comprised of any natural or synthetic elastomer or mixture thereof, that are inert to the fluid sample of interest and is flexible.

Preferably, the seal body comprises a qualitative stiffness, expressed as follows:

$$S^* = \frac{k}{a\rho_w D^2}$$

whereby S* is the non-dimensional stiffness coefficient, k is a force required to deflect the bellows a given length, a is the applied acceleration, D is the diameter of the seal body and $\rho_w$ is the density of water.

Desirably, the qualitative stiffness of the seal body is from about 0.00006 to about 190.

Preferably, the seal body may be subjected to a characteristic or radial deflection under an applied load, such as an axially applied load. The characteristic or radial deflection is defined as a change in length of the seal body relative to the change in cross section diameter of the seal body. Preferably, the seal body has a characteristic or radial deflection ratio of about 1.5 to about 3.5.

Preferably, the seal body when subjected to an applied load, such as centrifugation, to cause axial deformation of the seal body, the change in cross section diameter may be expressed as follows:

$$\frac{D_{before} - D_{during}}{D_{before}} \times 100\% = \Delta D_m$$

wherein $\Delta D_m$ is from about 5% to about 20%.

Therefore, a change in cross section diameter of the seal body is proportional to the undeflected cross section diameter of the seal body. Preferably, the proportion is from about 0.03 to about 0.20.

Desirably, the ballast is a substantially rigid moldable thermoplastic material such as polyvinyl chloride, polystyrene, polyethylene, polypropylene, polyethyleneterethalate, stainless steel, polyester and mixtures thereof that are inert to the fluid sample of interest. Most preferably, the ballast is a high density material. Preferably, the ballast is mounted around the second end of the bellows so as not to interfere with the central passageway of the separator. Most preferably, the ballast has a useful specific gravity from about 1.1 to about 7.9.

Desirably, the float is attached to the first end of the bellows whereby the float is in direct communication with the central passageway. Preferably, the float comprises small holes to bleed the air out of the central passageway of the separator. Most preferably, the float has a density from about 0.06 to about 0.95. Preferably, the float is a low density material such as polyethylene, polypropylene, polystyrene, foam, an air encapsulated system or a mixture of materials that reseal.

Preferably, the separator has an aggregate specific gravity of about 1.028 to about 1.09 g/cc so that the separator will come to rest under centrifugal force substantially at the border between the heavier and lighter phases of a fluid sample under consideration.

Preferably, the separator as a whole will function under load created by an applied acceleration from about 300 g to about 3000 g.

Preferably, the separator is initially secured to the top area of the tube and in alignment with the closure. The separator is fitted at the top end of the tube whereby the bellows of the separator, which provides the largest diameter of the separator in its undeformed state, may have an interference fit with the inner surface of the sidewall of the tube.

In use, a fluid sample enters the assembly by needle. The needle penetrates the closure and the float of the separator. The sample enters the assembly through the needle and through the central passageway of the bellows and then into the body of the tube. The needle is withdrawn from the assembly and the septum of the closure and the float reseals.

The assembly is then subjected to centrifugation. Forces exerted by the centrifuge cause the seal body to separate from the inner wall of the tube whereby the seal body elongates due to the difference in the buoyancy of the different elements of the separator. Under centrifugation, the separator migrates axially down the tube towards the closed end to the desired interface.

Sufficient movement of the separator will cause the separator to contact the blood. The ballast at the second end of the bellows moves axially downward under the centrifugal loading. The optional air bleed holes in the float or the resealable septum of the bellows serve to control the descent rate of the separator into the fluid sample.

Following immersion of the separator in the fluid, the float provides a buoyant upward force on the separator due to the displaced fluid. Simultaneously, the ballast provides an axial force downward on the separator. The combined forces stretch the seal body axially causing radial movement of the seal body inwardly which pulls it out of contact with the inner wall of the tube so that it is free to move axially without any frictional drag.

Therefore, a path is developed between the inner wall of the tube and the separator that permits the flow of the low-density component past the separator as it migrates down the tube. Migration of the separator terminates when it reaches the position between the lower density fluid component and higher density fluid or cellular/solid components, equal to its overall density. Upon terminating centrifugation, the seal body expands to its undeformed shape, sealing against the inner wall of the tube, thereby creating a barrier between the higher and lower density components of the sample fluid.

The separator's position at the top of the tube in alignment with the closure and the separator's float and central passageway, provides easy direct loading of the fluid sample into the tube. Thus, the fluid sample is easily delivered into the tube without exposing the uncentrifuged fluid sample to the outer surface area of the separator.

When the fluid sample is blood, the higher specific gravity portion that contains the cellular components is between the separator and the bottom of the tube after centrifugation. The lower specific gravity portion that contains the cell free serum or plasma fraction is between the float of the separator and the top of the tube.

The separator of the present invention comprises a useful range of parameters and there are two principle driving equations for defining the parameters:

$$\sigma_t V_t = \sigma_f V_f + \sigma_s V_s$$

(Conservation of Mass)

$$((\sigma_f - \sigma_t)V_f - (\sigma_s - \sigma_t)V_s)\rho_w = \frac{\delta \cdot \Delta D \cdot k}{a}$$

(Force Balance)

The following non-dimensional parameters may then be substitute into the force balance:

$$V_s^* = V_s/D^3; \quad V_f^* = V_f/D^3; \quad S^* = k/a\, \rho_w D^2$$

to arrive at:

$$((\sigma_f - \sigma_t)V_f^* - (\sigma_s - \sigma_t)V_s^*) = \frac{\delta \cdot \Delta D \cdot S^*}{D}$$

So as to scale prototypes to any size device, wherein the following are defined:

$\sigma_t$, $\sigma_f$, $\sigma_s$ are the specific gravities of the bellows, float and ballast, respectively;

$V_t$, $V_f$, $V_s$ are the volumes of the bellows, float and ballast, respectively;

$\rho_w$ is the density of water;

k is the separator spring constant;

a is the applied acceleration; and $\delta$ is the deflection ration defined by: $\Delta L/\Delta D$, where $\Delta L$ is the change in length.

The left side of the equation can be an infinite number of combinations of materials and geometries and if it is equal to the product of the right side it can be concluded that the device will function.

Desirable values for the right side of the equation are as follows:

$\delta = 1.5-3.5$ $\Delta D/D = 0.05$ to $0.2$ $S^* = 0.043$ to $0.220$.

Alternatively, the separator element may comprise an arrangement comprising a bellow member, a ballast member and a buoyancy or a float member.

Most preferably, the bellow member is made of a material and shape which allows deflections caused by opposing forces.

Most preferably, the buoyancy member has a component density whereby it has the capability of floating in serum of a blood sample. Preferably, the buoyancy member is made of a low density material such as foam or a material or mixture of materials so that it simulates a low density material such as foam.

Most preferably, the ballast member has a component density whereby it has the capability of sinking in a blood sample. Preferably, the ballast member is made of a high density material such as a substantially rigid moldable thermoplastic material. Such materials include but are not limited to polyvinyl chloride, polystyrene, polyethylene, polypropylene, stainless steel, polyester and mixtures thereof that are inert to the fluid sample of interest.

Most preferably, the separator element is arranged whereby the ballast member and buoyance members are connected and a central passageway extends through them. The bellow member covers the entrance to the central passageway and provides a pierceable barrier extending across the entrance to the central passageway.

Most preferably, the separator elements are assembled to create opposing forces to deflect the bellow member inwardly and allow it to move axially in the tube while under the proper loading.

Most preferably, the overall density of the separator is the target density $\sigma_t$ whereby to cause the device to position itself between the higher and lower density of a fluid sample.

Desirably, the bellow member may be comprised of any natural or synthetic elastomer or mixture thereof, that are inert to the fluid sample of interest and is flexible.

Preferably, the bellow member comprises a qualitative stiffness, expressed as follows:

$$S^* = \frac{k}{a \rho_w D^2}$$

whereby $S^*$ is the non-dimensional stiffness coefficient, k is a force required to deflect the bellow member a given length, a is the applied acceleration, D is the diameter of the bellow member and $\rho_w$ is the density of water.

Desirably, the qualitative stiffness of the bellow member is from about 0.00006 to about 190.

Preferably, the bellow member may be subjected to a characteristic or radial deflection under an applied load, such as an axially applied load. The characteristic or radial deflection is defined as a change in length of the bellow member relative to the change in cross section diameter of the bellow member. Preferably, the bellow member has a characteristic or radial deflection ratio of about 1.5 to about 3.5.

Preferably, the bellow member when subjected to an applied load, such as centrifugation, to cause axial deformation, the change in cross section diameter may be expressed as follows:

$$\frac{D_{before} - D_{during}}{D_{before}} \times 100\% = \Delta D_m$$

wherein $\Delta D_m$ is from about 5% to about 20%.

Therefore, a change in cross section diameter of the bellow member is proportional to the undeflected cross section diameter of the bellow member. Preferably, the proportion is from about 0.03 to about 0.20.

Desirably, the ballast member is a substantially rigid moldable thermoplastic material such as polyvinyl chloride, polystyrene, polyethylene, polypropylene, polyester and mixtures thereof that are inert to the fluid sample of interest. Most preferably, the ballast member is a high density material. Most preferably, the ballast member has a useful specific gravity from about 1.1 to about 7.9.

Desirably, the buoyancy member has a useful specific gravity from about 0.06 to about 0.95. Preferably, the buoyancy member is a low density material such as foam or encapsulated air.

Preferably, the separator has an aggregate specific gravity of about 1.028 to about 1.09 g/cc so that the separator will come to rest under centrifugal force substantially at the border between the heavier and lighter phases of a fluid sample under consideration.

Preferably, the separator as a whole will function under load created by an applied acceleration from about 300 g to about 3000 g.

Preferably, the separator is initially secured to the bottom recess of the closure. The separator is fitted with the closure whereby the bellows member of separator, which provides the largest diameter of the separator in its undeformed state, has a fit with the bottom recess of the closure. Alternatively, the separator may also be releasably positioned at the closed end of the tube.

In use, a fluid sample enters the assembly by needle. The needle penetrates the closure and the bellow member of the separator. The sample enters the assembly through the needle and through the central passageway of the separator and then into the body of the tube. The needle is withdrawn from the assembly and the septum of the closure and the bellow member reseals.

The assembly is then subjected to centrifugation. Forces exerted on the separator by the centrifuge cause the separator to separate from the closure or move from its initial position whereby the bellow member elongates as the separator migrates due to the forces pulling on it. Under centrifugation, the separator is released from the closure. The separator migrates axially down the tube towards the closed end.

Sufficient movement of the separator will cause the separator to contact the blood. Air trapped in the central passageway creates a buoyancy that could prevent further sinking of the separator into the fluid. However, the trapped air vents through a defect in the bellow member that is caused by the needle. This venting of air permits further movement of the separator into the fluid.

Following immersion of the separator in the fluid, the buoyancy member provides a buoyant upward force on the separator due to the displaced fluid. Simultaneously, the ballast member provides an axial force downward on the separator. The combined forces stretch the bellow member axially and pulls it out of contact with the closure so that it is free to move axially without any frictional drag.

Therefore, a path is developed between the inner wall of the tube and the separator that permits the flow of the low-density component past the separator as it migrates down the tube. Migration of the separator terminates when it reaches the position between the lower density fluid component and higher density fluid or cellular/solid components, equal to its overall density. Upon terminating centrifugation, the bellow member expands to its undeformed shape, sealing against the inner wall of the tube, thereby creating a barrier between the higher and lower density components of the sample fluid.

The separator's position at the top of the tube in alignment with the closure and the separator's penetrable bellows member and central passage, provides easy direct loading of the fluid sample into the tube. Thus, the fluid sample is easily delivered into the tube without exposing the uncentrifuged fluid sample to the outer surface area of the separator.

When the fluid sample is blood, the higher specific gravity portion that contains the cellular components is between the separator and the bottom of the tube after centrifugation. The lower specific gravity portion that contains the cell free serum or plasma fraction is between the bellows of the separator and the top of the tube.

The separator of the present invention comprises a useful range of parameters and there are two principle driving equations for defining the parameters:

$$\sigma_t V_t = \sigma_f V_f + \sigma_s V_s$$

(Conservation of Mass)

$$((\sigma_f - \sigma_t)V_f - (\sigma_s - \sigma_t)V_s)\rho_w = \frac{\delta \cdot \Delta D \cdot k}{a}$$

(Force Balance)

The following non-dimensional parameters may then be substitute into the force balance:

$$V_s^* = V_s/D^3; \quad V_f^* = V_f/D^3; \quad S^* = k/a\rho_w D^2$$

to arrive at:

$$((\sigma_f - \sigma_t)V_f^* - (\sigma_s - \sigma_t)V_s^*) = \frac{\delta \cdot \Delta D \cdot S^*}{D}$$

So as to scale prototypes to any size device, wherein the following are defined:

$\sigma_t$, $\sigma_f$, $\sigma_s$ are the specific gravities of the bellow member, buoyance member and ballast member, respectively;

$V_t$, $V_f$, $V_s$ are the volumes of the bellow member, buoyance member and ballast member, respectively;

$\rho_w$ is the density of water;

k is the separator spring constant;

a is the applied acceleration; and $\delta$ is the deflection ration defined by: $\Delta L/\Delta D$, where $\Delta L$ is the change in length.

The left side of the equation can be an infinite number of combinations of materials and geometries and if it is equal to the product of the right side it can be concluded that the device will function.

Desirable values for the right side of the equation are as follows:

$\delta = 1.5-3.5$ $\Delta D/D = 0.05$ to $0.2$ $S^* = 0.043$ to $0.220$.

The assembly of the present invention is advantageous over existing separation products that use gel. In particular the assembly of the present invention will not interfere with analytes as compared to gels that may interfere with analytes. Another attribute of the present invention is that the assembly of the present invention will not interfere with therapeutic drug monitoring analytes.

Most notably, is that the time to separate a fluid sample into separate densities is achieved in substantially less time with the assembly of the present invention as compared to assemblies that use gel.

Another notable advantage of the present invention is that fluid specimens are not subjected to low density gel residuals that are at times available in products that use gel.

A further attribute of the present invention is that there is no interference with instrument probes.

Another attribute of the present invention is that samples for blood banking tests are more acceptable than when a gel separator is used.

Another attribute of the present invention is that only the substantially cell-free serum fraction of a blood sample is exposed to the top surface of the separator, thus providing practitioners with a clean sample.

Additionally, the assembly of the present invention does not require any additional steps or treatment by a medical practitioner, whereby a blood or fluid sample is drawn in the standard fashion, using standard sampling equipment.

DETAILED DESCRIPTION

Figure 1:
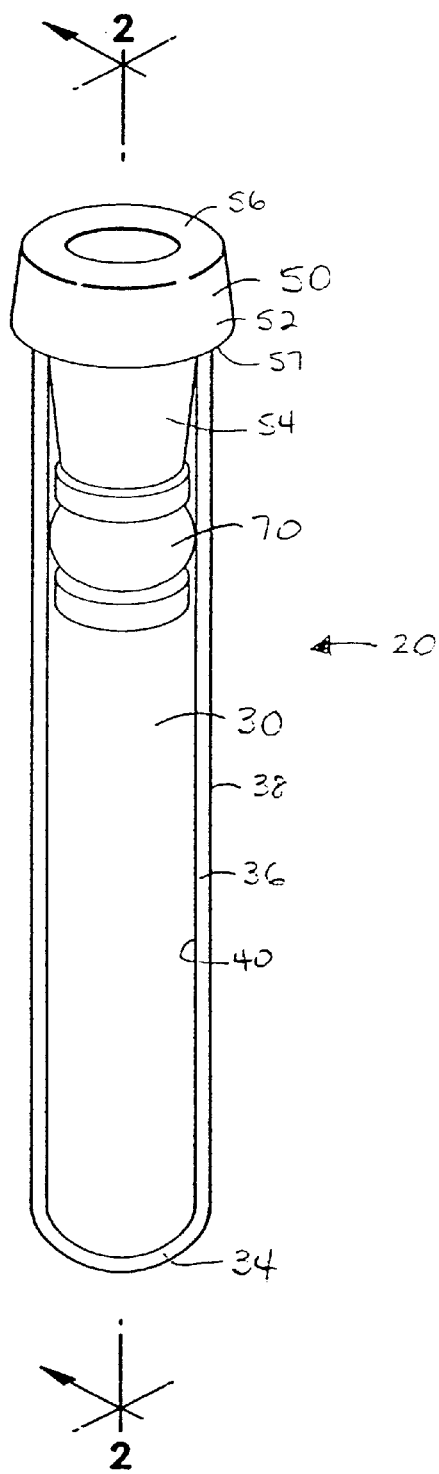
FIG. 1 is a perspective view of the assembly of the present invention.
Figure 2:
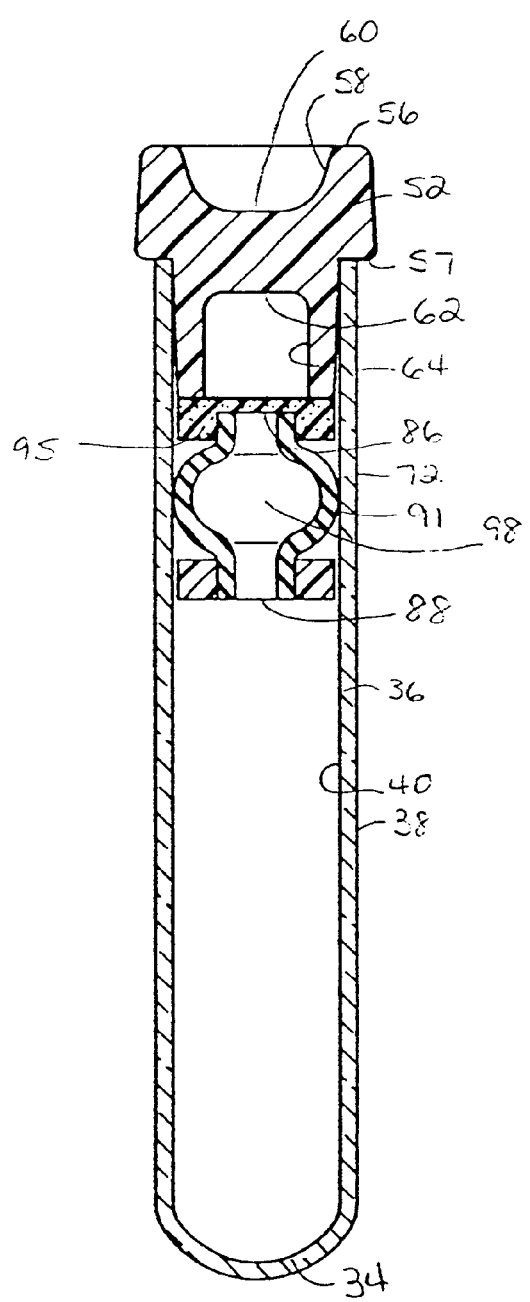
FIG. 2 is a longitudinal sectional view of the assembly of FIG. 1 taken along line 2—2 thereof.

The present invention may be embodied in other specific forms and is not limited to any specific embodiments described in detail, which are merely exemplary. Various other modifications will be apparent to and readily made by those skilled in the art without departing from the scope and spirit of the invention. The scope of the invention will be measured by the appended claims and their equivalents.

One embodiment of the present invention is illustrated in FIGS. 1 to 6, wherein assembly 20 comprises a tube 30, a closure 50 and a separator 70.

Tube 30 has an open end 32 that includes a top edge 33, a closed end 34 and a sidewall 36 extending between the open end and the closed end. Sidewall 36 has an outer surface 38 and an inner surface 40. Tube 30 defines a receptacle with a central axis "A".

Tube 30 is preferably made from a substantially transparent and rigid material. Suitable materials or the tube include glass, polystyrene, polyethyleneterephthalate, polycarbonate and the like.

Closure 50 is disposed to fit over open end 32 of tube 30. Closure 50 comprises an annular upper portion 52 which extends over top edge 33 of sidewall 36 and a lower annular portion or skirt 54 of lesser diameter than the annular upper portion 52 which extends into and forms an interference fit with inner surface 40 of sidewall 36 for maintaining stopper 50 in place in open end 32.

Annular upper portion 52 includes a top surface area 56, sidewall 58 that converges from surface area 56 towards upper well area 60. Well area 60 is most preferably a thin diaphragm or a self sealing septum for directing and receiving the point of a needle to be inserted into and through the stopper.

Lower annular skirt portion 54 defines a lower well 62, an inner wall surface, 64 an outer wall surface 66 and a bottom surface 68. Well area 60 and lower well area 62 define a thin diaphragm or self-sealing septum through which a needle may be inserted. The self sealing septum material allows penetration by a piercing element such as a needle and then reseals when the piercing element is withdrawn.

An annular ledge or abutment 57 separates annular upper portion 52 and lower annular portion 54.

Preferably, the closure maybe made of natural rubber elastomer, synthetic thermoplastic and thermoset elastomeric materials. Preferably, the closure is made of a resilient elastomeric material whereby the septum is self-sealing.

Figure 6:
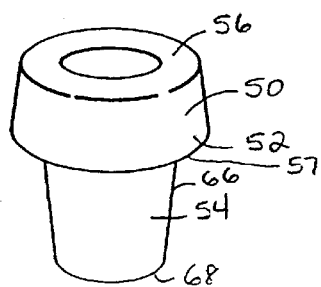
FIG. 6 is a perspective view of the unassembled elements of the assembly of the present invention.
Figure 6:
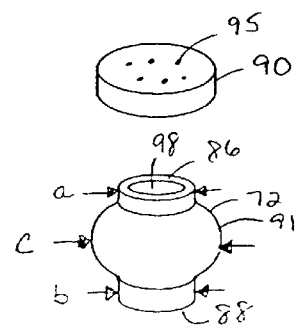
Figure 6:
Figure 6:
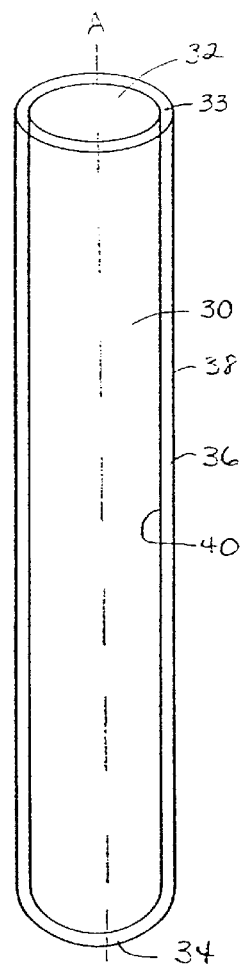
Figure 7:
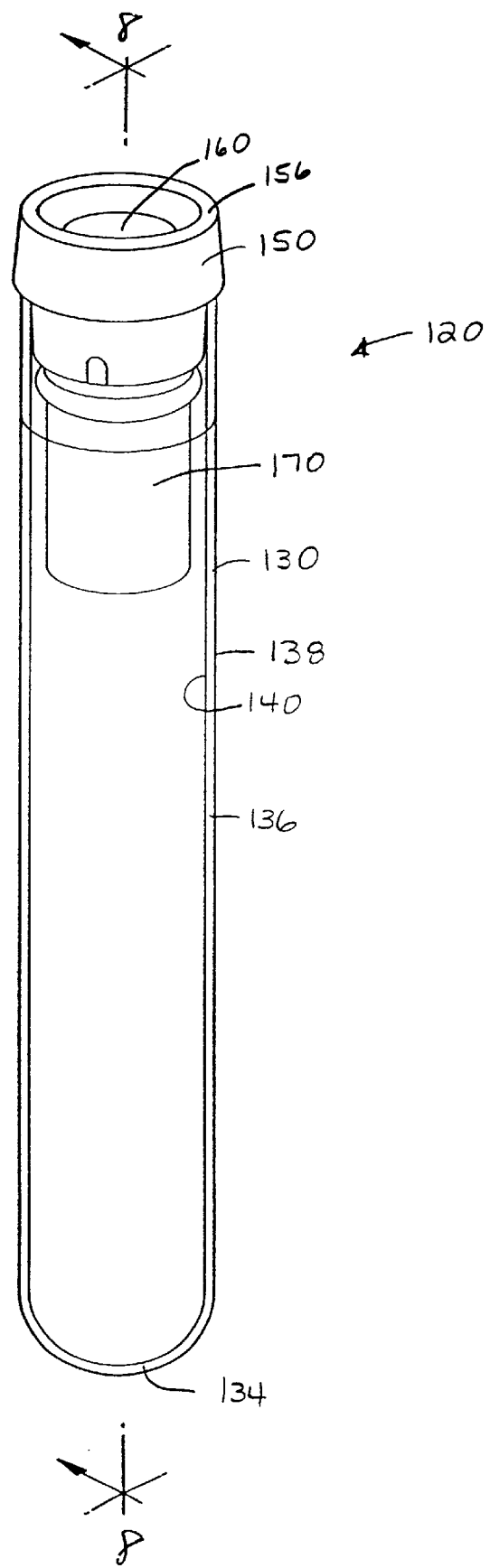
FIG. 7 is a perspective view of an alternate embodiment of the assembly of the present invention.
Figure 8:
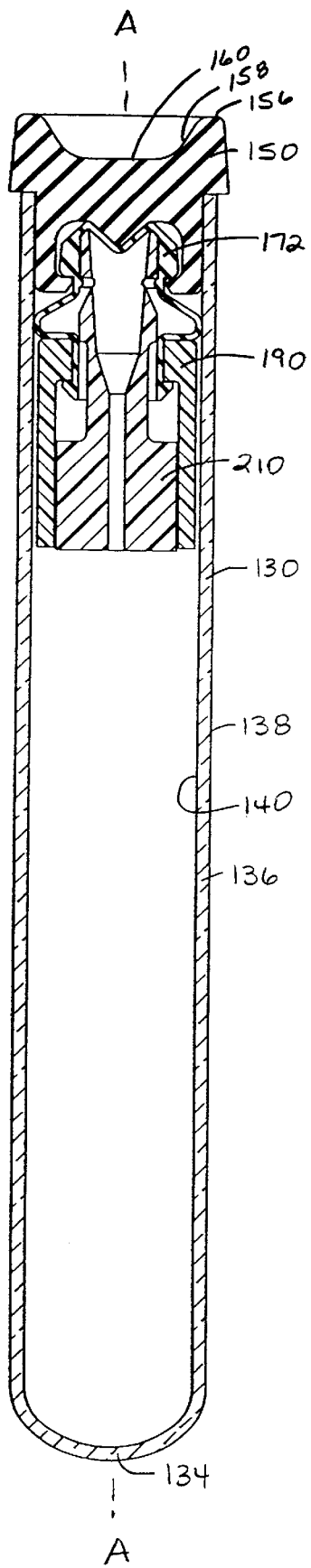
FIG. 8 is a longitudinal sectional view of the assembly of FIG. 7 taken along line 8—8 thereof.

As shown in FIG. 6, separator 70 comprises an elastic toroid or an elastic bellows 72, a low-density foam or a low density float 90 and a high-density sinker or a high density ballast 110. The components of the separator are formed from materials to exhibit a combined density less than the density of red blood cells, but greater than the density of serum of a blood sample.

Bellows 72 includes a top section 86, a bottom section 88, and a seal body 91 extending from the top section to the bottom section with a central passageway 98 extending between the ends and the seal body.

Low-density float 90 is located at top section 86 and ballast 110 is located at bottom section 88. Ballast 110 surrounds bottom section 88 without obstructing central passageway 98. Low density float 90 is at top section 86 and in direct alignment with central passageway 98.

Low-density float 90 comprises small holes 95 to bleed air out of central passageway 98 when in use.

The outside diameter "a" of top section 86 and the outside diameter "b" of bottom section 88 is less than the outside diameter "c" of the seal body when the seal body is in its undeformed position.

Seal body 91 of bellows 72 and the inner wall of the tube form an interference fit. The low-density float and the high-density ballast do not interfere with the inner wall of the tube.

Bellows 72 may be assembled by mounting float 90 over top section 86 and ballast 110 around the outer circumference of bottom end 88. The separator is then inserted into the open end of the tube. Sufficient radial interference causes the seal body to sealingly engage the inner tube sidewall.

Figure 3:
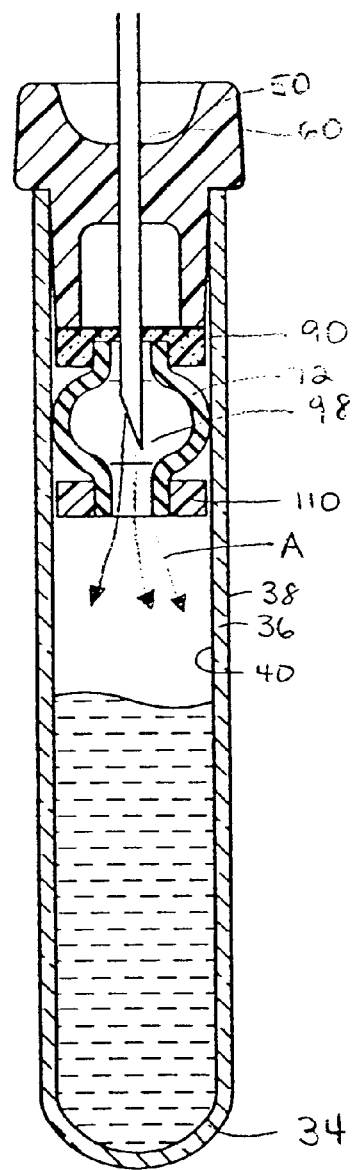
FIG. 3 is a longitudinal sectional view of the assembly of FIG. 1 taken along line 2—2 thereof illustrating fluid delivery into the assembly by a needle.

As shown in FIG. 3, a liquid sample A is delivered to the tube by a needle that penetrates closure 50 in upper well area 60 and the float. For purposes of illustration only, the liquid sample is blood. The liquid sample is delivered into the passageway of the separator so that the liquid sample is introduced between closed end 34 of the tube and the separator whereby the outer surface of all components of the separator are substantially free of any contact with the fluid sample.

Figure 4:
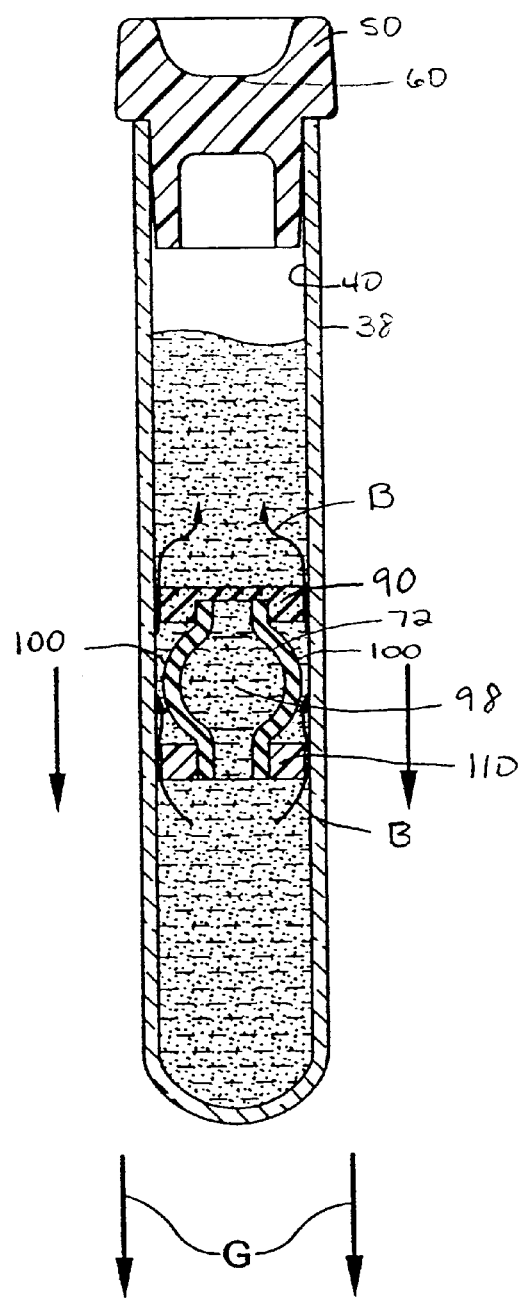
FIG. 4 illustrates that assembly under centrifugation and the release of the separator from the gripping means of the closure.

As shown in FIG. 4 when assembly 20 is subjected to centrifugation or axial centrifugation force, seal body 91 of separator 70 deflects, releases from the inner wall of the tube and descends towards closed end 34 of tube 30. As the separator descends, a lower specific gravity fraction B of fluid sample A moves upwardly past the separator. Air will be trapped in the passageway when the bottom section of the bellows contacts the fluid sample. This trapped air could restrict further downward movement of the separator. However, the small holes in the float defines a path through which trapped air may escape the passageway. Thus, separator 70 is permitted to sink into the fluid sample.

As the separator descends, seal body 91 of the separator deflects reducing its diameter and eliminating its interference fit with the inner wall of the tube. This opens up a path 100 between the tube and the separator, permitting the flow of the low-density component of the fluid past the separator as the separator migrates down the tube. The low residual density component inside the passageway 98 of the separator will migrate downwardly and upwardly past the separator.

Figure 5:
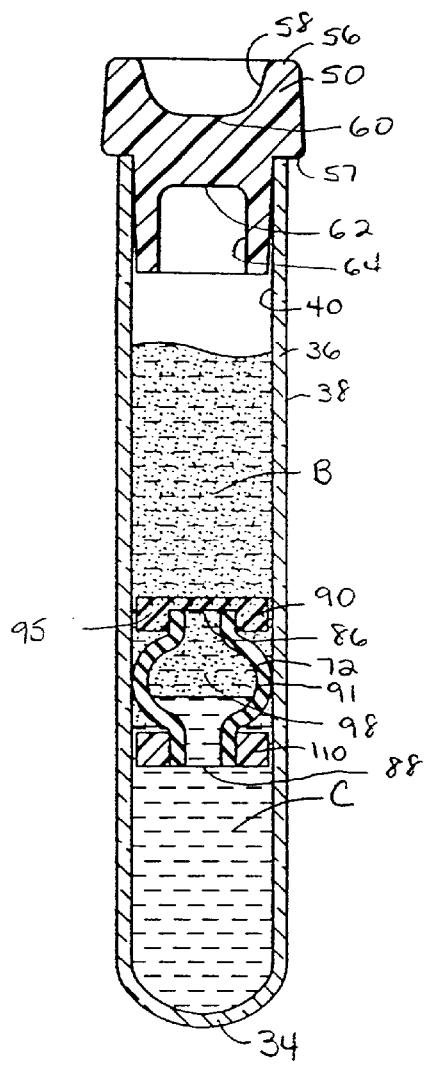
FIGS. 5 and 5A illustrates the assembly after centrifugation and the separation of the liquid sample into higher and lower specific gravities.
Figure 5A:
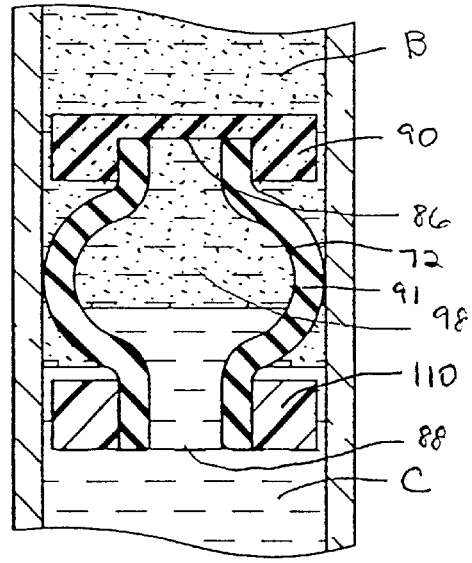

As shown in FIGS. 5 and 5A, after centrifugation is terminated, the absence of the centrifugal load will cause tubular portion to resiliently return toward an underformed condition and tightly seal with the inner wall of the tube as shown in FIG. 5. Thus, separator 70 serves as a divider between lower specific gravity portion B and higher specific gravity portion C of the liquid sample.

Tube 30 is compatible with most of the numerous additives used in sample collection tubes such as citrates, silicone, silicates, EDTA and the like that are used to condition the sample either to facilitate or retard clotting, or to preserve the sample for a particular analysis. It is within the purview of this invention that one or more additives may be used in the present invention for particular applications.

FIGS. 7–13 represent an alternative embodiment of the present invention.

As illustrated in FIGS. 7–13, the alternative embodiment comprises assembly 120, which comprises a tube 130, a closure 150 and a separator 170.

Tube 130 has an open end 132 that includes a top edge 133, a closed end 134 and a sidewall 136 extending between the open end and the closed end. Sidewall 136 has an outer surface 138 and an inner surface 140. Tube 130 defines a receptacle with a central axis "A".

Tube 130 is preferably made from a substantially transparent and rigid material. Suitable materials or the tube include glass, polystyrene, polyethyleneterephthalate, polycarbonate and the like.

Closure 150 is disposed to fit over open end 132 of tube 130. Closure 150 comprises an annular upper portion 152 which extends over top edge 133 of sidewall 136 and a lower annular portion or skirt 154 of lesser diameter than the annular upper portion 152 which extends into and forms an interference fit with inner surface 140 of sidewall 136 for maintaining stopper 150 in place in open end 132.

Annular upper portion 152 includes a top surface area 156, sidewall 158 that converges from surface area 156 towards upper well area 160. Well area 160 is most preferably a thin diaphragm or a self sealing septum for directing and receiving the point of a needle to be inserted into and through the stopper.

Lower annular skirt portion 154 defines a lower well 162, an inner wall surface, 164 an outer wall surface 166 and a bottom surface 168. Well area 160 and lower well area 162 define a thin diaphragm or self-sealing septum through which a needle may be inserted. The self sealing septum material allows penetration by a piercing element such as a needle and then reseals when the piercing element is withdrawn.

An annular ledge or abutment 157 separates annular upper portion 152 and lower annular portion 154. Located on bottom surface 168 of lower annular portion 154 are gripping means 169 that are used to initially align and hold the separator.

Preferably, the closure maybe made of natural rubber elastomer, synthetic thermoplastic and thermoset elastomeric materials. Preferably, the closure is made of a resilient elastomeric material whereby the septum is self-sealing.

Figure 12:
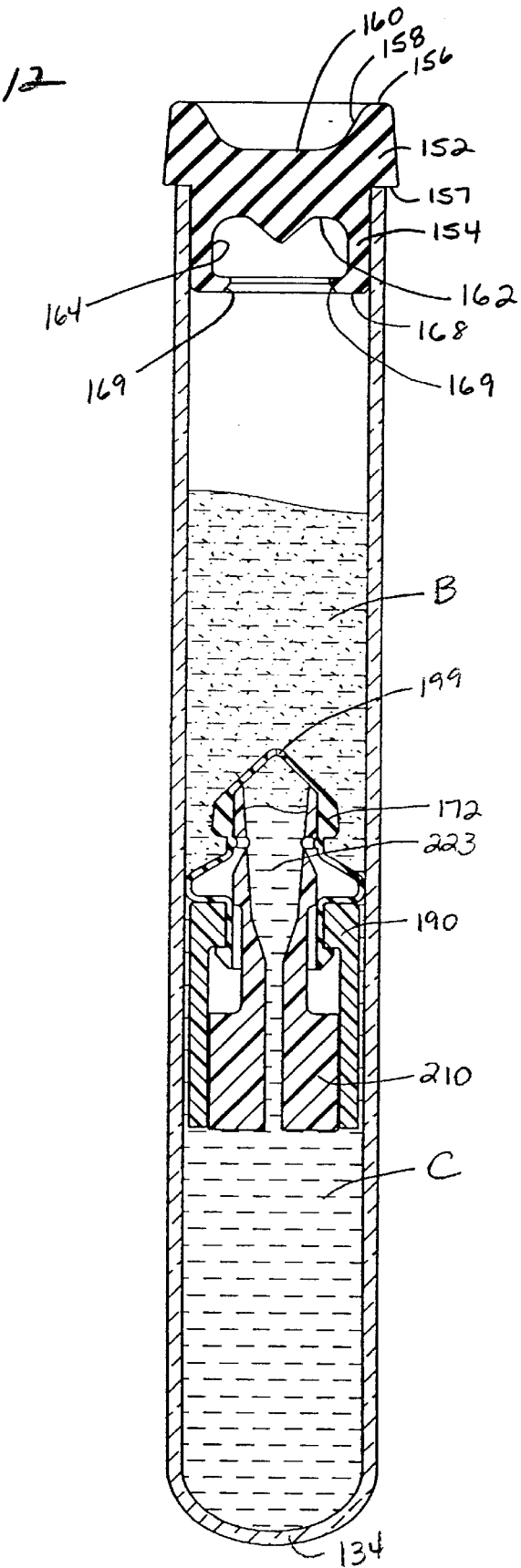
FIG. 12 illustrates the assembly after centrifugation and the separation of the liquid sample into higher and lower specific gravities.
Figure 13:
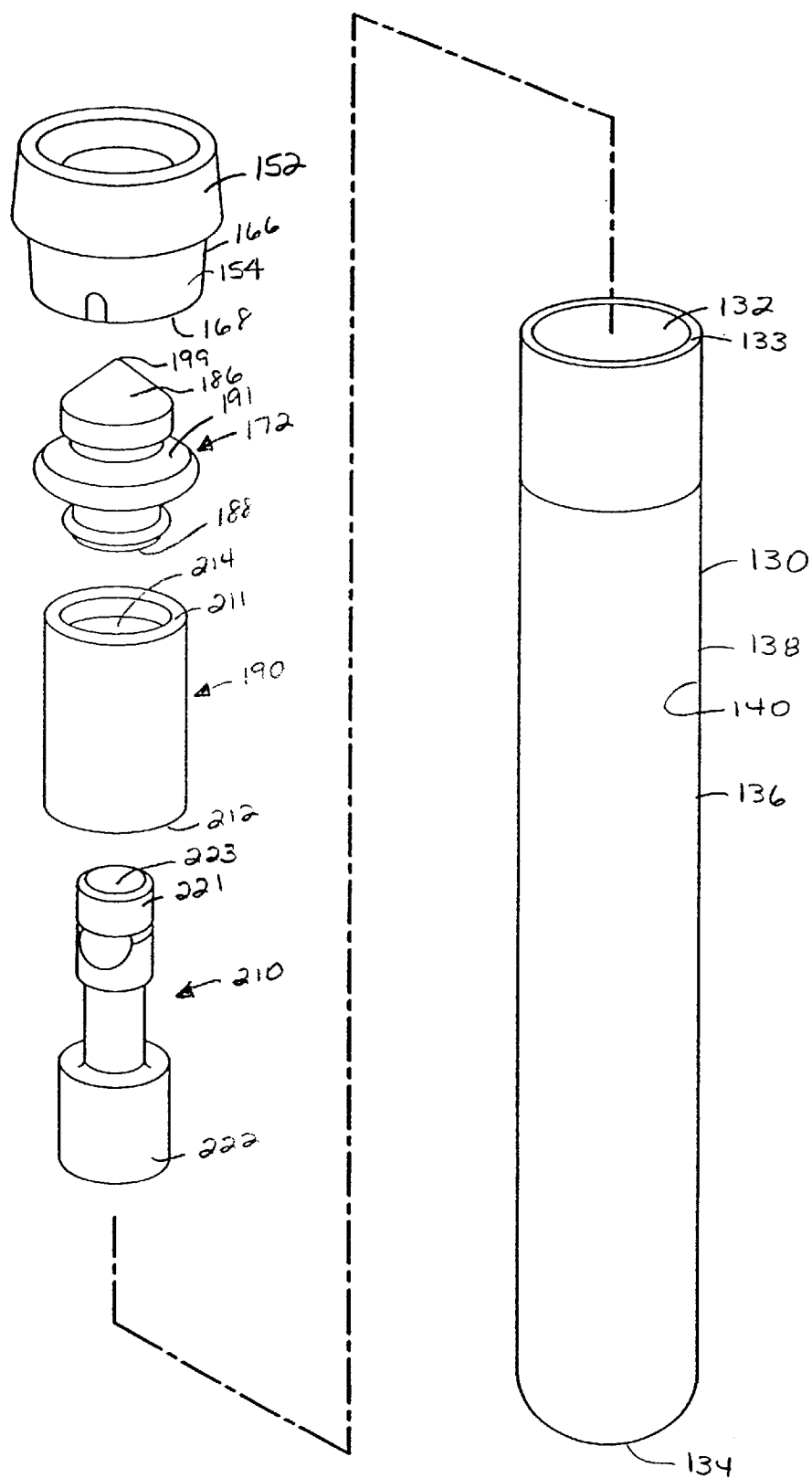
FIG. 13 is a perspective view of the unassembled elements of the assembly of the present invention.

As shown in FIGS. 12 and 13, separator 170 comprises a bellow member 172, a low-density buoyance or float member 190 and a high-density sinker or ballast member 210. The components of the separator are formed from materials to exhibit a combined density less than the density of red blood cells, but greater than the density of serum of a blood sample.

Buoyancy member 190 comprises a top section 211 a bottom section 212 and a central passageway 214 extending continuously between the ends.

Bellow member 172 comprises a rupturable elastomeric material such as Kraton copolymer, a urethane or PVC. Bellow member 172 includes a bottom 188, a top 186, a seal body 191 extending between the top and bottom, an initially conically convex top wall 199 at top 186.

Ballast member 210 comprises a cylindrical sidewall 220 extending from a top end 221 to a bottom end 222 and a central passageway 223 extending between the top and bottom ends.

The separator is assembled whereby ballast member 210 is fitted with bellow member 172 top end 221 of ballast member 210 is fitted within convex top wall 199 and then the bottom end of the ballast member is joined with top section 211 of the buoyance member whereby central passageway 223 extends from top wall 199 through to bottom end 222 of the ballast member 210.

Figure 9:
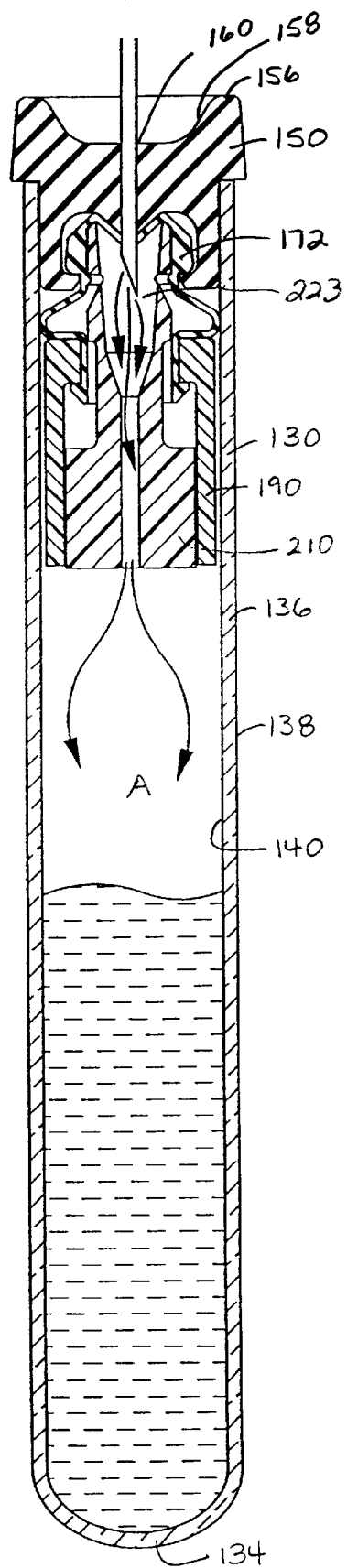
FIG. 9 is a longitudinal sectional view of the assembly of FIG. 7 taken along line 8—8 thereof illustrating fluid delivery into the assembly by a needle.

As shown in FIG. 9, a liquid sample A is delivered to the tube by a needle that penetrates closure 150 in upper well area 160 and conical top wall 199 of bellow member 172. For purposes of illustration only, the liquid sample is blood.

The liquid sample is delivered into the passageway of the separator so that the liquid sample is introduced between closed end 34 of the tube and the separator whereby the outer surface of all components of the separator are substantially free of any contact with the fluid sample.

Figure 10:
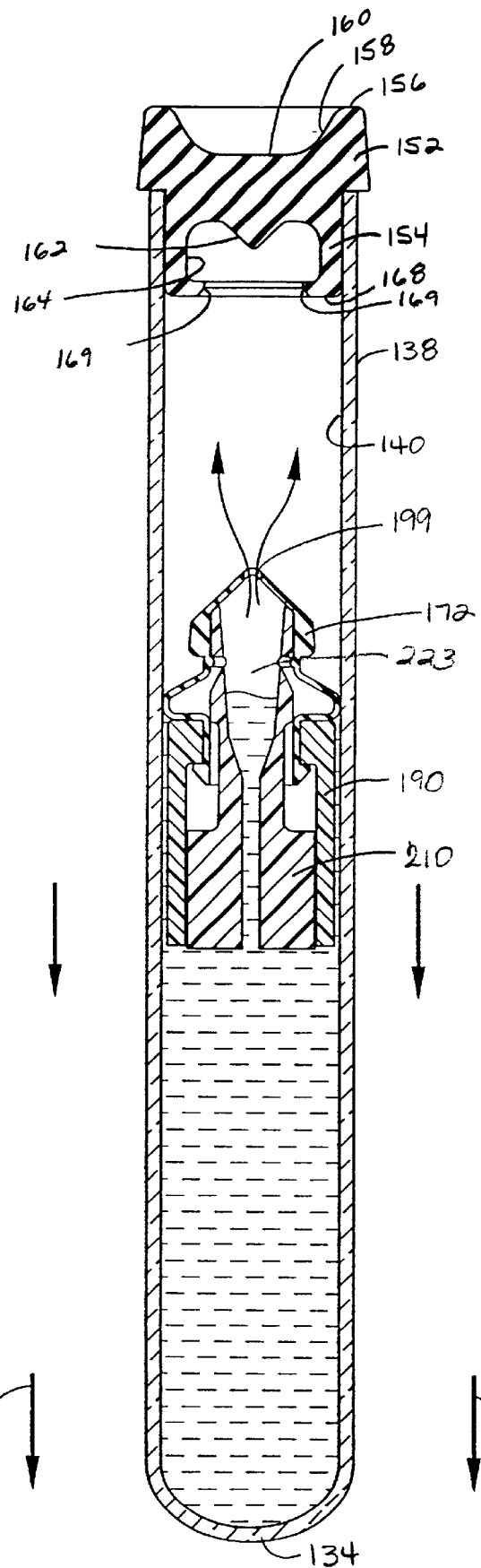
FIGS. 10 and 11 illustrates that assembly under centrifugation and the release of the separator from the gripping means of the closure.
Figure 11:
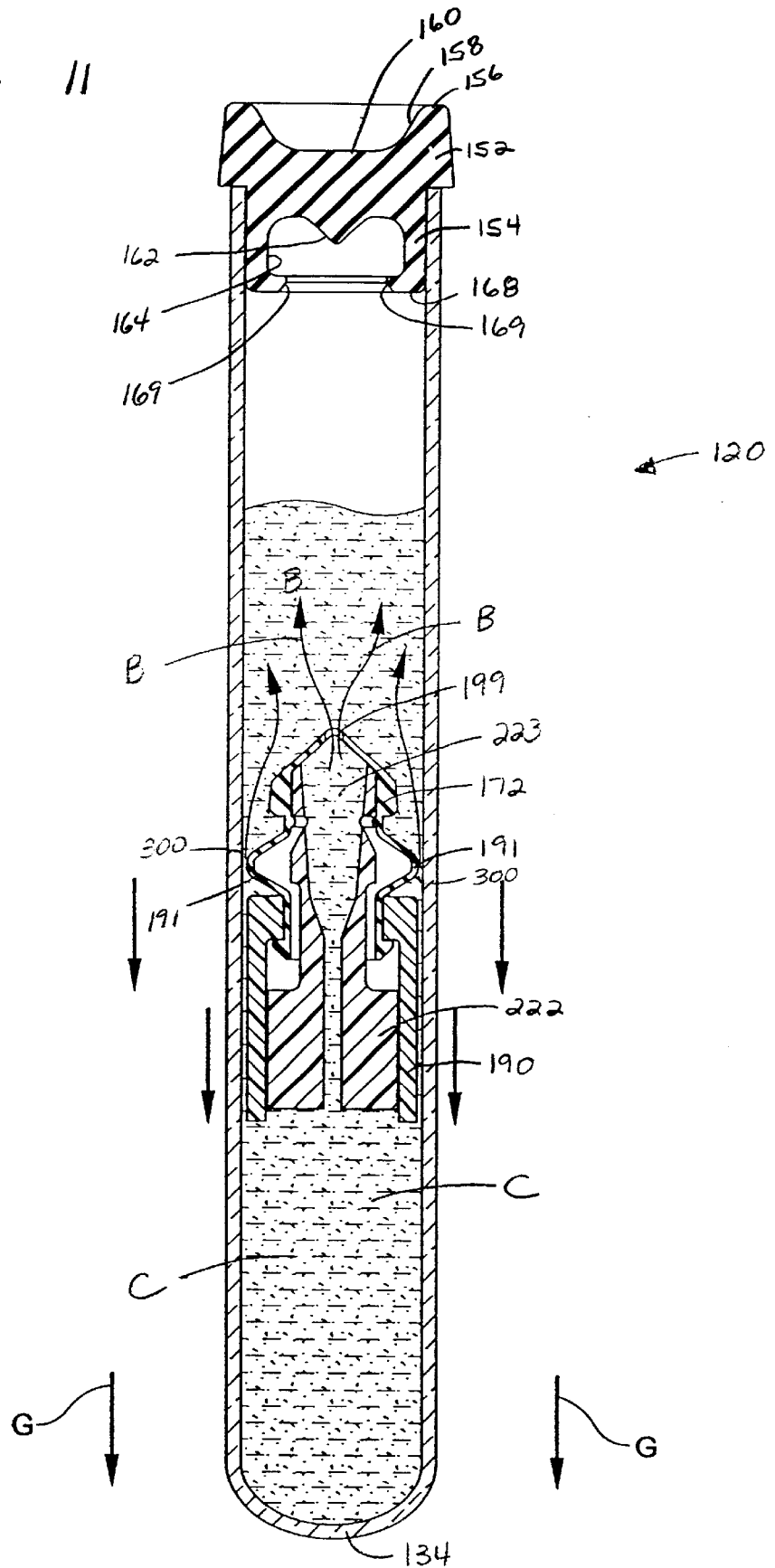

As shown in FIGS. 10 and 11 when assembly 120 is subjected to centrifugation or axial centrifugation force, seal body deflects, whereby the separator release from the closure and descends towards closed end 134 of tube 130. As the separator descends, a lower specific gravity fraction B of fluid sample A moves upwardly past the separator.

As the separator descends, seal body 191 of the separator deflects reducing its diameter and eliminating its interference fit with the inner wall of the tube. This opens up a path 300 between the tube and the separator, permitting the flow of the low-density component of the fluid past the separator as the separator migrates down the tube. The low residual density component inside central passageway 223 of the separator will migrate downwardly and upwardly past the separator.

After centrifugation is terminated, the absence of the centrifugal load will cause the seal body to resiliently return toward an undeformed condition and tightly seal with the inner wall of the tube as shown in FIG. 12. Thus, separator 170 serves as a divider between lower specific gravity portion B and higher specific gravity portion C of the liquid sample.

Tube 130 is compatible with most of the numerous additives used in sample collection tubes such as citrates, silicone, silicates, EDTA and the like that are used to condition the sample either to facilitate or retard clotting, or to preserve the sample for a particular analysis. It is within the purview of this invention that one or more additives may be used in the present invention for particular applications.

EXAMPLE 1

An assembly of the present invention was compared to a commercially available product that uses a gel as the separator mechanism. Ten samples of the present invention and ten samples of the commercial product were used. The commercial product was VACUTAINER Brand PLUS SST® tubes (trademarks of and manufactured by Becton Dickinson and Co., Franklin Lakes, N.J.) (Catalog No. 367988).

The separator of the present invention comprising a bellows, a float, and a ballast were made from separate molds using an injection molding process. The bellows was made from a GLS Dynaflex® G6725 thermoplastic elastomer compound (DYNAFLEX® is a trademark of and manufactured by GLS Corporation, Cary, Ill.) having a specific gravity of 0.889. The float was made from a pre-compounded blend of Eastman LDPE 1870-A and 3M Scotchlite™ glass bubbles S60 (SCOTCHLITE™ is a trademark of and manufactured by 3M, St. Paul, Minn.) to yield a specific gravity of about 0.809. The ballast was made from Eastar® MN058 copolyester (EASTAR® is a trademark of and manufactured by Eastman Chemical Company, Kingsport, Tenn.) with a specific gravity of about 1.335.

The separator was assembled with a closure designed to receive the separator and then with a tube. The assembly was assembled and evacuated to a level which yield 8.5 ml blood draw.

A blood sample was directed into each of the ten samples of the present invention and the commercial product. Each sample was placed in a floor model centrifuge and centrifuged at 1000 RCF for five minutes. The separator of the present invention and that of the commercial product migrated into position and formed a seal between the serum and the red blood cells/clot. The serum analytes were then measured and reported in Table 1. In clinical chemistry, analytes (components in human blood) are measured and used to aid in the diagnosis and monitoring of diseased states in human patients. The results of Table 1 show that the present invention, which has a non-gel separator, yields comparable serum analyte values as to the commercial product that contains a gel as the separator.

TABLE 1

| Analyte N = 10 | Glucose | BUN | Creatinine | Sodium |
|---|---|---|---|---|
| Present Invention | 124.2 | 14.5 | 1.0 | 138.1 |
| PLUS SST | 124 | 14.5 | 0.96 | 138.1 |

| Analyte N = 10 | Potassium | Chloride | CO2 | Magnesium |
|---|---|---|---|---|
| Present Invention | 4.4 | 101.5 | 22.9 | 1.65 |
| PLUS SST | 4.35 | 100.7 | 23.7 | 1.63 |

| Analyte N = 10 | Calcium | Inorganic phosphorous | Total Protein | Albumin |
|---|---|---|---|---|
| Present Invention | 9.3 | 3.53 | 7.15 | 4.3 |
| PLUS SST | 9.3 | 3.57 | 7.15 | 4.2 |

| Analyte N = 10 | Bilirubin | Alkaline Phosphatase | LDH, Total | GGT | AST |
|---|---|---|---|---|---|
| Present Invention | 0.7 | 65.2 | 163.5 | 23.2 | 26 |
| PLUS SST | 0.6 | 63.5 | 141.7 | 23.1 | 25.1 |

| Analyte N = 10 | ALT | Uric Acid | Iron | Triglyceride | Cholesterol |
|---|---|---|---|---|---|

TABLE 1-continued

| Prototype | 25 | 4.3 | 99.9 | 127.1 | 199.6 |
|---|---|---|---|---|---|
| PLUS SST | 25 | 4.2 | 97.5 | 125.6 | 197.2 |

EXAMPLE 2

The separator of the present invention comprising a bellows, a float, and a ballast, were made from separate molds using an injection molding process. The bellows was made from GLS Dynaflex® G6725 thermoplastic elastomer compound (DYNAFLEX® is a trademark of and manufactured by GLS Corp., Gary, Ill.) having a specific gravity of 0.889. The float was made from a pre-compounded blend of Dow LDPE 993I and Uniroyal Chemical Celogen® 754A to yield a specific gravity of 0.782. The ballast was made from Eastar® MN058 copolyester (ESTAR® is a trademark of and manufactured by Eastman Chemical Company, Kingsport, Tenn.) with a specific gravity of 1.335. The separator was assembled with a closure designed to receive the separator and then with a tube. The assembly was assembled and evacuated to a level which yield 8.5 ml blood draw.

A blood sample was directed into each sample. Then each sample was placed in a floor model centrifuge and centrifuged for three minutes. The separator of the present invention and that of the commercial product migrated into position and formed a seal between the serum and the red blood cells/clot. The serum analytes were then measured and reported in Table 2.

commercial product was VACUTAINER Brand PLUS SST® tubes (trademarks of a manufactured by Becton Dickinson and Co., Franklin Lakes, N.J., Catalog No. 367988). The separator of the present invention comprising a bellows, a float, and a ballast, were made from separate molds using an injection molding process. The bellows was made from GLS Dynaflex® G6730 thermoplastic elastomer compound (DYNAFLEX® is a trademark of an manufactured by GLS Corp., Gary, Ill.) having a specific gravity of 0.889. The float was made from a pre-compounded blend of Dow LDPE 993I and Uniroyal Chemical Celogen® 754A to yield a specific gravity of 0.782. The ballast was made from pigmented Eastar® MN058 copolyester (EASTAR® is a trademark of and manufactured by Eastman Chemical Co., Kingsport, Tenn.) with a specific gravity of 1.335. The separator was positioned at the bottom of the tube.

A blood sample was directed into each of the samples of the present invention and the commercial product. Then each sample was placed in a floor model centrifuge and centrifugal for ten minutes. The separator of the present invention and that of the commercial product migrates into position and forms a seal between the plasma and the red blood cells. The plasma analytes were measured arid reported in Table 3.

TABLE 2

| Analyte | Phosphlipid | BUN | Creatinine | Creatine Kinase | Sodium |
|---|---|---|---|---|---|
| Present Invention | 209.9 | 13.23 | 0.71 | 108.9 | 139.7 |
| PLUS SST | 208.2 | 13.3 | 0.715 | 107.7 | 139.7 |

| Analyte | Potassium | Chloride | UIBC | Cholinesterase | Calcium |
|---|---|---|---|---|---|
| Present Invention | 4.1 | 101.5 | 280.9 | 283.4 | 9.4 |
| PLUS SST | 4.1 | 101.5 | 277.2 | 281.8 | 9.4 |

| Analyte | Inorganic phosphorous | Total Protein | Albumin | Direct Bilirubin | Total Bilirubin |
|---|---|---|---|---|---|
| Present Invention | 4.1 | 7.3 | 4.41 | 0.165 | 0.683 |
| PLUS SST | 3.4 | 7.2 | 4.39 | 0.163 | 0.685 |

| Analyte | Bilirubin | Alkaline Phosphatase | LDH, Total | GGT | LAP | AST |
|---|---|---|---|---|---|---|
| Present Invention | 0.165 | 184.6 | 325.2 | 17.95 | 56.1 | 23 |
| PLUS SST | 0.163 | 182.6 | 323.9 | 18 | 56.1 | 22.8 |

| Analyte | Amylase | ALT | Uric Acid | Iron | Triglyceride | Cholesterol |
|---|---|---|---|---|---|---|
| Present Invention | 197.2 | 21.3 | 56.1 | 89.5 | 94 | 183 |
| PLUS SST | 194.8 | 21.5 | 56.1 | 89.5 | 91.5 | 182.2 |

EXAMPLE 3

An assembly of the present invention was compared to a commercially available product that has a gel component as the separator mechanism. A sample of the present invention and a sample of the commercial product were used. The

TABLE 3

|  | Initial | 24 hrs | Initial | 24 hrs | Initial | 24 hrs | Initial | 24 hrs |
|---|---|---|---|---|---|---|---|---|
|  | Glucose | | BUN | | Creatinine | | Sodium | |
| Present Invention Tube N = 3 | 51 | 38 | 19 | 19 | 1.1 | 1.1 | 140 | 143 |
| PLUS PST Tube N = 1 | 49 | 29 | 19 | 20 | 1.1 | 1.2 | 142 | 142 |
|  | Potassium | | Chloride | | Calcium | | Phosphorus, Inorganic | |
| Present Invention Tube N = 3 | 4.1 | 4.4 | 104 | 104 | 9.3 | 9.7 | 3.7 | 3.6 |
| PLUS PST Tube N = 1 | 4.0 | 4.2 | 104 | 104 | 9.5 | 9.6 | 3.9 | 3.9 |
|  | Protein, Total | | Albumin | | Cholesterol | | Bilirubin, Total | |
| Present Invention Tube N = 3 | 7.8 | 7.8 | 4.6 | 4.7 | 176 | 179 | 1.0 | 0.8 |
| PLUS PST Tube N = 1 | 7.7 | 7.7 | 4.6 | 4.7 | 175 | 173 | 1.0 | 0.8 |
|  | Alkaline Phosphatase | | LDH | | GGT | | AST | |
| Present Invention Tube N = 3 | 0.97 | 0.67 | 153 | 166 | 12 | 13 | 23 | 22 |
| PLUS PST Tube N = 1 | 1.0 | 0.8 | 149 | 170 | 13 | 13 | 23 | 22 |
|  | ALT | | Uric Acid | | Iron, Total | | Triglycerides | |
| Present Invention Tube N = 3 | 17 | 18 | 3.8 | 4.1 | 351 | 352 | 82 | 87 |
| PLUS PST Tube N = 1 | 17 | 17 | 3.7 | 4.0 | 344 | 353 | 81 | 83 |

What is claimed is:

1. An assembly for separating a fluid sample into a higher specific gravity phase and a lower specific gravity phase comprising:
   a separator element comprising a bellows, a float and a ballast;
   said bellows comprising opposed first and second ends, a seal body extending between said ends and a central passageway extending through said bellows;
   said float is mounted to said first end of said bellows; and
   said ballast is mounted to said second end of said bellows.

2. The assembly of claim 1, wherein said bellows has a specific gravity of about 0.8 to about 1.2 and the material of said bellows has a 50% tensile modulus of about 100 psi to about 500 psi.

3. The assembly of claim 1, wherein said seal body has a qualitative stiffness of:

$$S^* = \frac{k}{a \rho_w D^2}$$

whereby k is a force required to deflect said bellows a given length; a is an applied acceleration; D is the diameter of the seal body; and $\rho_w$ is the density of water;
   said seal body has a deflection ratio of about 1.5 to about 3.5 when said seal body is subjected to a characteristic or radial deflection under an applied load; and
   said seal body changes from about 5% to about 20% of its original cross sectional diameter when said seal body is subjected to an applied load.

4. The assembly of claim 2, wherein said ballast has a specific gravity from about 1.1 to about 7.9.

5. The assembly of claim 2, wherein said float comprises small holes to bleed the air out of said central passageway of said separator and a resealable septum and has a density of about 0.06 to about 0.95 g/cc.

6. The assembly of claim 1, wherein said separator has a combined specific gravity of about 1.028 to about 1.09.

7. An assembly for separating a fluid sample into a higher specific gravity phase and a lower specific gravity phase comprising:
   a tube comprising an open end, a closed end, an inner diameter, an outer diameter and a sidewall extending between said open end and said closed end;
   said sidewall comprising an outer surface and an open surface;
   a closure disposed in said open end of said tube;
   a separator element movable axially in said tube under the action of centrifugal force;
   said separator element providing selectively an annular seal and an open passage there around in response to pressure differentials in said tube above and below said separator;
   said separator element comprising a bellows, a float and a ballast;
   said bellows comprising opposed first and second ends, a seal body extending between said ends for selectively providing an interference fit and an open passage with said inner surface of said sidewall of said tube in response to alternating equal and different pressures above and below said separator and a central passageway extending through said bellows to direct said fluid sample into said assembly;
   said float is mounted to said first end of said bellows and has a specific gravity less than the specific gravity of said fluid sample; and said ballast is mounted to said second end of said bellows and has a specific gravity greater than the specific gravity of said fluid sample.

8. The assembly of claim 7, wherein said separator is located at said open end of said tube by an interference fit between said seal body and said inner diameter of said tube.

9. The assembly of claim 7, wherein said bellows has a specific gravity of about 0.8 to about 1.2 and the material of said bellows has a 50% tensile modulus of about 100 psi to about 500 psi.

10. The assembly of claim 7, wherein said seal body has a qualitative stiffness of:

$$S^* = \frac{k}{a\rho_w D^2}$$

whereby k is the force required to deflect said bellows a given length; a is the applied acceleration; D is the diameter of the seal body; and $\rho_w$ is the density of water said seal body has a deflection ratio of about 1.5 to about 3.5 when said seal body is subjected to a characteristic or radial deflection under an applied load; and said seal body changes from about 5% to about 20% of its original cross sectional diameter when said seal body is subjected to an applied load.

11. The assembly of claim 7, wherein said ballast has a specific gravity of about 1.1 to about 7.9.

12. The assembly of claim 7, wherein said float comprises small holes to bleed the air out of said central passageway of said separator and a resealable septum and a density of about 0.06 to about 0.95 g/cc.

13. The assembly of claim 7, wherein said separator has a combined specific gravity of said separator is about 1.028 to about 1.09.

14. A method for separating a fluid sample into a higher specific gravity phase and a lower specific gravity phase, comprising the steps of:
   (a) providing a tube comprising an open end, a closed end, an inner diameter, an outer diameter and a sidewall extending between said open end and said closed end and comprising an outer surface and an inner surface;
   (b) providing a closure disposed in said open end of said tube comprising a resealable septum;
   (c) providing a separator element comprising a bellows, a float and a ballast whereby said bellows comprises opposed first and second ends, a seal body extending between said ends for selectively providing an interference fit and an open passage with said inner surface of said sidewall of said tube in response to alternating equal and different pressures above and below said separator, and a central passageway extending through said bellows; said float comprising a resealable septum is mounted to said first end of said bellows and said ballast is mounted to said second end of said bellows;
   (d) providing said separator element in said tube whereby said seal body comprises an interference fit with said inner wall;
   (e) providing a needle that penetrates said closure and said float;
   (f) delivering a fluid sample to said tube whereby said sample enters through said needle and through said central passageway of said bellows and then into said body of said tube;
   (g) removing said needle from said assembly whereby said septum of said closure and said float reseals;
   (h) subjecting said tube with said separator element to centrifugation whereby said seal body separates from said inner wall of said tube and said separator migrates axially in said tube whereby the low density component of the sample migrates down the tube; and
   (i) terminating said centrifugation whereby said seal body expands to its underformed shaping, sealing against said inner wall of said tube, thereby creating a barrier between said higher and lower density components of said fluid sample.

15. A separator for separating a fluid sample into a higher specific gravity phase and a lower specific gravity phase comprising:
   a separator element comprising a bellow member, a ballast member and a buoyancy member;
   said bellow member comprising a bottom section, a top section, a seal body extending between said top section and said bottom section and an initially conically convex top wall at said top section;
   said buoyancy member comprising a top section, a bottom section and a central passageway extending continuously between said ends;
   said ballast member comprising a top end, a bottom end, a sidewall extending between said top end and said bottom end and a central passageway surrounded by said sidewall extending between said top end and said bottom end; and
   whereby said ballast member is fitted within said convex top wall of said bellow member and said buoyancy member is joined to surround said ballast member whereby a central passageway extends from said convex top wall to said bottom end of said ballast member.

16. An assembly for separating a fluid sample into a higher specific gravity phase and a lower specific gravity phase comprising:
   a tube comprising an open end, a closed end, an inner diameter, an outer diameter and a sidewall extending between said open end and said closed end;
   said sidewall comprising an outer surface and an inner surface;
   a closure disposed in said open end of said tube comprising means to engage said bellows member of said separator;
   a separator element movable axially in said tube under the action of centrifugal force;
   said separator element providing selectively an annular seal and an open passage there around in response to pressure differentials in said tube above and below said separator;
   said separator element comprising a bellow member, a ballast member and a buoyancy member;
   said bellows member, a bottom section, a top section, a seal body extending between said top section and said bottom section and an initially conically convex top wall at said top section;
   said buoyancy member comprising a top section, a bottom section and a central passageway extending continuously between said ends; and
   said ballast member comprising a top end, a bottom end, a sidewall extending between said top end and said bottom end and a central passageway surrounded by said sidewall extending between said top end and said bottom end.

17. A method for separating a fluid sample into a higher specific gravity phase and a lower specific gravity phase, comprising the steps of:

(a) providing a tube comprising an open end, a closed end, an inner diameter, an outer diameter and a sidewall extending between said open end and said closed end and comprising an outer surface and an inner surface;

(b) providing a separator element comprising a bellow member, a ballast member and a buoyancy member; said bellows member, a bottom section, a top section, a seal body extending between said top section and said bottom section and an initially conically convex top wall at said top section; said buoyancy member comprising a top section, a bottom section and a central passageway extending continuously between said ends; and said ballast member comprising a top end, a bottom end, a sidewall extending between said top end and said bottom end and a central passageway surrounded by said sidewall extending between said top end and said bottom end;

(c) providing a closure disposed in said open end of said tube comprising means to engage said bellows member of said separator;

(d) engaging said separator with said closure;

(e) providing a needle that penetrates said closure and said float;

(f) delivering a fluid sample to said tube whereby said sample enters through said needle and through said central passageway of said bellows and then into said body of said tube;

(g) removing said needle from said assembly whereby said septum of said closure and said float reseals;

(h) subjecting said tube with said separator element to centrifugation whereby said seal body separates from said inner wall of said tube and said separator migrates axially in said tube whereby the low density component of the sample migrates down the tube; and (i) terminating said centrifugation whereby said seal body expands to its underformed shaping, sealing against said inner wall of said tube, thereby creating a barrier between said higher and lower density components of said fluid sample.

* * * * *

UNITED STATES PATENT AND TRADEMARK OFFICE
Certificate

Patent No. 6,479,298 B1                                                                               Patented: November 12, 2002

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Henry F. Miller, Clifton, NJ; Robert J. Losada, Astoria, NY; Fu-Chung Lin, Wayne, NJ; Paul C. DiCesare, Easton, CT; and Jeffrey P. Radziunas, Wallingford, CT.

Signed and Sealed this Thirty-first Day of August 2004.

JILL WARDEN
*Supervisory Patent Examiner*
Art Unit 1743